United States Patent [19]
Satyavathi et al.

[11] Patent Number: 5,986,138
[45] Date of Patent: Nov. 16, 1999

[54] PROCESS FOR PRODUCING ALKYLATED AROMATIC AMINES WITH HIGH SELECTIVITY USING NEW CATALYST

[75] Inventors: Bankupalli Satyavathi; Akash Narhar Rao Patwari; Uday Triambakraj Bhalerao, all of Hyderabad, India

[73] Assignee: Council of Scientific & Industrial Research, New Delhi, India

[21] Appl. No.: 09/047,719

[22] Filed: Mar. 25, 1998

[51] Int. Cl.⁶ .................................................. C07C 209/00
[52] U.S. Cl. ........................................... 564/402; 564/404
[58] Field of Search ..................................... 564/402, 409

*Primary Examiner*—Samuel Barts
*Attorney, Agent, or Firm*—Ladas & Parry

[57] ABSTRACT

The present invention relates to a process for the preparation of alkylated aromatic amines which comprises reacting an aromatic amine selected from aniline, toludine, xylidine, N-methyl aniline, N-ethyl aniline, m-ethyl aniline, p-ethyl aniline, o-ethyl aniline with a primary or secondary alcohol selected from ethanol, methanol, isopropyl alcohol in the presence of attalpulgite impregnated with combination of iron oxide and oxides selected from transition metals of the periodic table as a catalyst prepared by the method described and claimed in our co-pending U.S. patent application Ser. No. 09/047,718 at atmospheric pressure and at a temperature in the range of 300–400° C. and recovering the desired amine by conventional methods.

6 Claims, No Drawings

PROCESS FOR PRODUCING ALKYLATED AROMATIC AMINES WITH HIGH SELECTIVITY USING NEW CATALYST

The present invention relates to a process for the preparation of alkylated aromatic amines. This invention particularly relates to an improved process for the selective preparation of ortho and N-alkylated aromatic amines. The present invention more particularly relates to an improved process for the preparation of 2,6-Dialkylamines such as 2,6-Diethylaniline or dimethylaniline and N-alkylated amines such as N-ethyl or N-methyl anilines. The process of the present invention involves the reaction of an aromatic amine and a primary or a secondary alcohol in the presence of a new catalyst containing attapulgite impregnated with a combination of iron oxide and the oxides selected from transition metals of the periodic table. The reaction is effected under moderate conditions of atmospheric pressure and low temperatures.

BACKGROUND OF THE INVENTION

Attapulgite used in the catalyst is a fibrous clay. The chemical analysis of attapulgite clay shows the presence of oxides such as $SiO_2$, $Al_2O_3$, $MgO$, $Na_2O$, $Fe_2O_3$ and water along with traces of nickel, chromium, zinc, copper, lead, tin, vanadium and silver and the composition of Attalpulgite in form of mole percent is as follows:

$SiO_2$ - - - 55.03%

$Al_2O_3$ - - - 10.24%

$Fe_2O_3$ - - - 03.53%

$MgO$ - - - 10.49%

$K_2O$ - - - 00.47%

$H_2O^-$ - - - 09.73%

$H_2O_+$ - - - 10.13%

We have carried out extensive research in respect of the use of attapulgite for catalyzing chemical reactions. Some of the other uses of attapulgite are listed here:

It is used as a polymerization catalyst, in refining vegatable oils and fats, as a carrier for granular and powdered agricultural chemicals (insecticides and herbicides), in petroleum refining, decolourising, neutralising, brightening and for desulphurization.

It is also used as an oil base and water base foundry sand binders, latex paint thickener, gelling agent, polishing-suspending agent for abrasives and as a wax emulsion stabilizer.

We have observed during our research that attapulgite can be used as catalyst for alkylation reaction. In our continued work developing attapulgite as a catalyst for selective alkylation of aromatic amines we have observed that when attapulgite is impregnated with a combination of iron oxide and oxides selected from transition metals of the periodic table, the effect of alkylation is greatly enhanced. The catalyzing activity of the resultant catalyst for the alkylation reaction, in particular for ortho and N-alkylation is found to be enchanced.

Alkylated aromatic amines are useful in a broad range of applications. Particularly ortho-alkylated aromatic amines are used as intermediates for producing dyes, Insecticides, resin stabilizers, rubber compounding ingredients and the like.

In the Japanese patent publication No. 47-24014/72 a method has been described in which aromatic amines such as aniline and the like are reacted with alkyl aluminium halide, followed by reaction of the resultant mixture with olefins. In Japanese patent No. 50-137934/75 a method has been described in which aromatic amines are reacted with lower olefins in the presence of a catalyst consisting of aluminium anilide and halogenated hydrocarbons. The above mentioned processes have advantages that the reaction activity and selectivity are high, but due to the involvement of very high temperatures and pressures there is a disadvantage that the reaction apparatus suitable for the conditions has to be used, and since a substantial amount of the catalyst is used, post treatment for removing the catalyst from the reaction mixture is troublesome.

Other prior art processes for producing ortho alkylated aromatic amines include methods like that proposed in U.S. Pat. No. 2,814,646 in which an aromatic amine is reacted with olefins under heating in the presence of an aluminium anilide catalyst. The disadvantage of this process is that the reaction activity is low, although the selectivity in the product is high. In U.S. Pat. No. 4,351,958 a process for producing ortho-alkylated aromatic amines in which, an aromatic amine is reacted with olefins, has been described at a temperature in the range of 200–500° C. with reaction pressure from 1–30 kg/cm² and a catalyst comprising iron oxide as a main constituent. A variety of catalysts have been tried by this method and the maximum selectivity of 2,6-dialkylaniline is reported as 51.6% under optimum conditions.

N-Alkylated aromatic amines are useful in a broad range of applications. They are used as raw materials for synthesis of organic chemicals, and as intermediates for producing dyes, in agrochemical industries like fertilizers, as resin stabilizers, rubber compounding ingredients and the like.

The vapor phase catalytic reaction of aniline and ethanol is the method of choice for the industrial production of N-ethylaniline. In European patent EP 39,061 a method has been described wherein aromatic amines are prepared treating olefins with ammonia and a primary or a secondary amine in presence of Ruthenium or ferric compound dissolved in liquid phase solvent. The temperatures and pressures employed being 100–250° C. and 1–12000 psig.

In Japanese patent 58,146,534 a method has been described in which N-alkylated anilines are prepared by alkylation of $H_2NC_6H_{5-n}X_n$ with alcohols/ethers in gas phase in presence of S ion, Ti and Zr catalysts.

Other prior arts for producing N-ethylaniline include both liquid phase methods and vapor phase methods. These processes differ mostly in the type of catalyst used. The liquid phase processes produce N-ethylaniline with equal quantities of the diethylated products, and are still in vogue.

Several combinations of the catalyst have been reported, in particular alumina promoled with different metal oxides appears to have been widely employed. Zeolites have been used extensively as catalysts for the production of N-alkylated anilines. Bauxite is also proved to be a good catalyst for this reaction.

The main object of the present invention is to provide an improved process for the preparation of alkylated aromatic amines.

Another object of the present invention is to provide an improved process for the preparation of ortho-alkylated and N-alkylated aromatic amines. Yet another object of the present invention is to provide an improved process for the preparation of ortho-ethyl or ortho-methyl or N-ethyl or N-methyl amines. The invention is based on the findings that when attapulgite is impregnated with a combination of iron oxide and oxides selected from the transition metals of the periodic table, the activity of the resultant catalyst is enhanced for selective alkylation of the aromatic amines.

DETAILED DESCRIPTION OF THE INVENTION

Accordingly the present invention provides an improved process for the preparation of alkylated aromatic amines which comprises; reacting an aromatic amine with a primary alcohol in the presence of attapulgite impregnated with a combination of iron oxide and oxides selected from the transition metals of the periodic table as catalyst prepared by the method described and claimed in our copending U.S. application Ser. No. 09/047,718 (corresponding to Indian Patent Application No.2620/Del/95) at atmospheric pressure and at a temperature in the range of 300–400° C. and recovering the alkylated amines by known methods.

The composition of the catalyst as used in the process of our present invention is comprises 1–75% of iron oxide, 1–10% of titanium metal oxide and the balance being attapulgate useful for the preparation of alkylated aromatic amines and is prepared by the process, which comprises impregnating attapulgite with a combination of iron oxide and oxides selected from transition metals of the periodic table, converting the resultant catalyst to the desired form, drying the catalyst and calcining by known methods.

The amine used in the process of present invention may be selected from aniline, o-toluidinen m-toluidine, p-toluidine, p-ethylaniline, m-ethylaniline, O-ethylaniline, 2,3 Xylidine, N-ethylaniline, and M-methylaniline.

The alcohol used in the process of present invention may be selected from methanol, ethanol, n-propanol, n-butyl alcohol, iso-butyl alcohol, and iso-propyl alcohol. The amount of alcohol used may be in the range of 1–10 moles of alcohol based on 1 mole of the aromatic amine used. After completion of the reaction the ortho-alkylated aromatic amine may be seperated from the reaction mixture by distillation.

The recovered alcohol and aromatic amine can be recycled. As side reactions N,N-dialkylamines may be produced in quantities of 10–20%. These byproducts may be recycled to produce the desired alkylated amine under the same reaction conditions, thus in effect causing a quantitative conversion of the amine to the desired alkylated aromatic amines.

The metal oxides used for impregnation may be such as oxides of typical metallic elements such as aluminium oxide, silicon oxide, germanium dioxide, magnesium oxide, and oxides of the transition metals such as copper oxide, titanium oxide, zirconium oxide, chromium oxide and the like.

In our corresponding U.S. patent application Ser. No. 09/047,718 (corresponding to Indian Patent Application No.2620/Del/95) described and claimed a process for the preparation of the catalyst which is employed in the process of the present invention. Table 1 shows that the increase in percentage of Iron Oxide from 0–60% enhances the conversion of aniline and Table 2 shows the enhancement in the selectivity of the catalyst towards ring alkylation. The variation is shown in tables 1 and 2.

TABLE 1

% IRON OXIDE IN CATALYST VS CONVERSION AT DIFFERENT TEMPERATURES

| % $Fe_2O_3$ | $X_{AO}$ (330° C.) | $X_{AO}$ (350° C.) | $X_{AO}$ (370° C.) | $X_{AO}$ (390° C.) | $X_{AO}$ (410° C.) |
|---|---|---|---|---|---|
| 0 | 36.14 | 55.00 | 56.30 | 49.10 | 22.10 |
| 15 | 46.20 | 60.00 | 60.00 | 63.00 | 51.00 |
| 25 | 48.20 | 71.40 | 73.40 | 68.90 | 49.60 |
| 35 | 48.40 | 70.50 | 78.00 | 69.70 | 49.60 |
| 45 | 49.06 | 76.40 | 79.10 | 70.10 | 50.90 |
| 55 | 51.00 | 86.40 | 90.30 | 69.90 | 52.20 |
| 60 | 53.30 | 86.10 | 92.20 | 80.50 | 61.50 |
| 70 | 52.10 | 83.30 | 90.50 | 82.90 | 69.40 |

$X_{AO}$: OVERALL CONVERSION OF ANILINE

TABLE 2

% IRON OXIDE IN CATALYST VS SELECTIVITY OF PRODUCTS

| % $Fe_2O_3$ | % Select MEA | % Select N, NDEA | % Select 2,6 DEA |
|---|---|---|---|
| 0 | 54.85 | 12.26 | 16.23 |
| 15 | 72.10 | 14.88 | 13.02 |
| 25 | 65.44 | 20.81 | 13.65 |
| 35 | 66.24 | 19.38 | 14.38 |
| 45 | 70.03 | 13.36 | 16.61 |
| 55 | 64.25 | 13.37 | 22.38 |
| 60 | 62.54 | 09.57 | 27.89 |
| 70 | 57.18 | 15.84 | 26.98 |

MEA: MONOETHYLANILINE
N,NDEA: N,N-diethylaniline
2,6-DEA: 2,6-diethylaniline

TABLE 3

| Temp (°C.) | $GeO_2$ (1%) | $Al_2O_3$ (1%) | ZnO (1%) | MgO (1%) | $Cr_2O_3$ (1%) | $SnO_2$ (1%) | $SnO_2$ (2%) |
|---|---|---|---|---|---|---|---|
| SHOWS THE EFFECT OF PROMOTERS ON THE CONVERSION AND SELECTIVITY OF PRODUCT COMPONENTS BY FIXING THE PERCENTAGE OF IRON OXIDE IN THE CATALYST TEMPERATURE VS SELECTIVITY OF MONOETHYLANILINE (USING DIFFERENT PROMOTERS) ||||||||
| 350 | 74.95 | 82.48 | 68.42 | 44.14 | 58.70 | 52.42 | 34.77 |
| 370 | 67.00 | 61.10 | 66.85 | 42.45 | 57.55 | 47.44 | 17.65 |
| 390 | 65.00 | 59.84 | 63.77 | 39.98 | 49.12 | 52.31 | 21.53 |
| 410 | 60.00 | 54.79 | 63.57 | 39.49 | 45.58 | 50.05 | 20.58 |
| TEMPERATURE VS SELECTIVITY OF N,N-DIETHYLANILINE (USING DIFFERENT PROMOTERS) ||||||||
| 350 | 16.00 | 11.73 | 15.75 | 09.84 | 18.80 | 05.24 | 09.68 |
| 370 | 17.00 | 28.85 | 14.84 | 09.82 | 18.85 | 05.88 | 10.24 |
| 390 | 18.65 | 29.55 | 16.56 | 10.00 | 20.56 | 06.86 | 12.33 |
| 410 | 17.24 | 30.48 | 16.11 | 08.86 | 19.32 | 06.47 | 10.10 |
| TEMPERATURE VS SELECTIVITY OF 2,6-DIETHYLANILINE (USING DIFFERENT PROMOTERS) ||||||||
| 350 | 09.05 | 05.84 | 15.83 | 09.64 | 23.03 | 42.32 | 55.53 |
| 370 | 16.00 | 10.05 | 18.31 | 09.95 | 23.35 | 46.68 | 72.11 |
| 390 | 16.35 | 10.61 | 19.67 | 09.90 | 30.32 | 40.83 | 66.14 |
| 410 | 22.76 | 14.82 | 20.32 | 11.00 | 35.10 | 43.48 | 46.88 |

The details of the invention is described in the following examples which are presented by way of illustration only and should not be construed to limit the scope of the present invention.

EXAMPLES

Example 1

50 gms of attapulgite containing iron oxide and tin oxide as catalyst is packed into a reactor and heated to 350° C. A liquid mixture of aniline and ethanol having a mole ratio of 1:5 is fed at a rate of 60 ml/hr whereby the reaction is effected. The product components so obtained are separated by distillation. The conversion of the amine is 65% and the yield of the ortho-alkylated aromatic amine is 44%.

Example 2

50 gms of attapulgite containing iron oxide and tin oxide as catalyst is packed into a reactor and heated to 370° C. A liquid mixture of aniline and ethanol having a mole ratio of 1:5 is fed at a rate of 60 ml/hr whereby the reaction is effected. The conversion of the amine is 69% and the yield of the ortho-alkylated aromatic amine is 50%.

Example 3

50 gms of attapulgite containing iron oxide and magnesium oxide as catalyst is packed into a reactor and heated at 370° C. A liquid mixture of aniline and ethanol having a mole ratio of 1:5 is fed at a rate of 60 ml/hr whereby the reaction is effected. The product components so obtained are separated by distillation. The conversion of the amine is 52% and the yield of the ortho-alkylated aromatic amine is 5%.

Example 4

50 gms of attapulgite containing iron oxide and Zinc oxide as catalyst is packed into a reactor and heated to 370° C. A liquid mixture of aniline and ethanol having a mole ratio of 1:5 is fed at a rate of 60 ml/hr whereby the reaction is effected. The product components arc separated by distillation. The conversion of the amine is 58% and the yield of the ortho-alkylated aromatic amine is 11%.

Example 5

50 gms of attapulgite containing iron oxide and Chromium oxide as catalyst is packed into a reactor and heated to 370° C. A liquid mixture of aniline and ethanol having a mole ratio of 1:5 is fed at a rate of 60 ml/hr whereby the reaction is effected. The product components are separated by distillation. The conversion of the amine is 57% and the yield of the ortho-alkylated aromatic amine is 14%.

Example 6

50 gms of attapulgite impregnated with iron oxide and germanium dioxide as catalyst is packed into a reactor and heated to 375° C. A liquid mixture of aniline and ethanol having a mole ratio of 1:5 is fed at a rate of 60 ml/hr whereby the reaction is effected. The product components are separated by distillation. The conversion of aniline obtained is 87% and the yield of N-alkylanililne is 75%.

Example 7

50 gms of attapulgite impregnated with iron oxide and germanium dioxide as catalyst is packed into a reactor and heated to 350° C. A liquid mixture of aniline and ethanol having a mole ratio of 1:5 is fed at a rate of 60 ml/hr whereby the reaction is effected.

The product components are separated by distillation. The conversion of aniline obtained is 80% and the yield of N-alkylaniline is 64%.

Example 8

50 gms of attapulgite containing iron oxide and magnesium oxide as catalyst is packed into a reactor and heated to 370° C. A liquid mixture of aniline and ethanol having a mole ratio of 1:5 is fed at a rate of 60 ml/hr whereby the reaction is effected. The product components are separated by distillation. The conversion of the amine is 52% and the yield of the N-alkylated aromatic amine is 22%.

Example 9

50 gms of attapulgite impregnated with iron oxide and chromium oxide as catalyst is packed into reactor and heated to 375° C. A liquid mixture of aniline and ethanol having a mole ratio of 1:5 is fed at a rate of 60 ml/hr whereby the reaction is effected. The product components are separated by distillation. The conversion of aniline obtained is 57% and the yield of N-alkylaniline is 33%.

Example 10

50 gms of attapulgite impregnated with iron oxide and zinc oxide as catalyst is packed into reactor and heated to 370° C. A liquid mixture of aniline and ethanol having a mole ratio of 1:5 is fed at a rate of 60 ml/hr whereby the reactiom is effected. The product components are separated by distillation. The conversion of aniline obtaied is 58% and the yield of N-alkylaniline is 38%.

We claim:

1. A process for the preparation of alkylated aromatic amines which comprises reacting an aromatic amine selected from the group consisting of aniline, toluidine, xylidine, N-methyl aniline, N-ethyl aniline, m-ethyl aniline, p-ethyl aniline, and o-ethyl aniline with a primary or secondary alcohol selected from the group consisting of ethanol, methanol, isopropyl alcohol in the presence of attalpulgite impregnated with a combination of iron oxide and oxides selected from the group consisting of transition metals of the periodic table as a catalyst, said catalyst prepared by a process which comprises impregnating attapulgite with a combination of iron oxide and oxides selected from the group consisting of transition metals of the periodic table, converting the resultant catalyst to the desired form, drying the catalyst and calcining at atmospheric pressure and at a temperature in the range of 300–400° C. and recovering the alkylated amine.

2. A process as claimed in claim 1, wherein the amount of alcohol used is in the range of 1–10 moles based on 1 mole of the amine used.

3. A process as claimed in claim 1, wherein the amount of amine used is in the range of 1–3 moles.

4. A process as claimed in claim 1, wherein the alkylated aromatic amine produced is separated by distillation.

5. A process as claimed in claim 1, wherein by-products formed are re-cycled.

6. A process as claimed in claim 1 wherein the catalyst used is attapulgite impregnated with iron oxide and transition metal oxide selected from the group consisting of magnesium oxide, zinc oxide, chromium oxide and germanium oxide.

* * * * *